United States Patent [19]

Pearce et al.

[11] 4,366,103

[45] Dec. 28, 1982

[54] DEODORIZED ORGANOTHIOPHOSPHOROUS AND EMULSIFIABLE CONCENTRATES THEREOF

[75] Inventors: David A. Pearce, Edison; John J. Mehok, Clinton, both of N.J.

[73] Assignee: Rhone-Poulenc Agrochimie, Lyon, France

[21] Appl. No.: 217,971

[22] Filed: Dec. 19, 1980

[51] Int. Cl.$^3$ .............................................. C07C 9/201
[52] U.S. Cl. ...................................... 260/967; 260/989
[58] Field of Search ................................ 260/967, 989

[56] References Cited

U.S. PATENT DOCUMENTS 3,341,632  9/1967  Wu ........................................ 260/967

FOREIGN PATENT DOCUMENTS 1211085  11/1970  United Kingdom ................ 260/989

Primary Examiner—Anton H. Sutto
Attorney, Agent, or Firm—Morgan, Finnegan, Pine, Foley & Lee

[57] ABSTRACT

Organothiophosphorous compounds, e.g., Merphos, which contain or develop malodorous mercaptan impurities during storage, are protected against such odor development by the addition of minor amounts (0.1 to 10%) of a ketone, especially in the presence of a catalyst such as cuprous chloride or p-toluene sulfonic acid in a concentration range of 0.01 to 0.1%. Formulated products are also claimed.

8 Claims, No Drawings

DEODORIZED ORGANOTHIOPHOSPHOROUS AND EMULSIFIABLE CONCENTRATES THEREOF

BACKGROUND OF THE INVENTION

1. Field of the Invention

This invention is directed to stabilizing at low odor levels S,S,S-trialkylphosphorotrithioites and other organothiophosphorus compounds.

2. Description of the Prior Art

Various materials have been proposed to make or suppress odor in certain organothiophosphorus compounds. In U.S. Pat. No. 3,925,519, for example, it is disclosed that aliphatic anyydrides will suppress odor formation in S,S,S-trialkylphosphorotrithioite nematocides and insecticides. Insofar as is now known, it has not been proposed to use ketones for this purpose.

SUMMARY OF THE INVENTION

This invention provides a substantially deodorized composition comprising an organothiophosphorus compound especially one having the structure: $P(SR)_3$, wherein R is $C_1$–$C_8$ alkyl and a minor stabilizing amount of a $C_3$–$C_{10}$ aliphatic or cycloaliphatic ketone. It also provides a method of stabilizing against malodor development such organophosphorus compound that comprises adding thereto a minor stabilizing amount of a $C_3$–$C_{10}$ aliphatic or cycloaliphatic ketone.

DESCRIPTION OF SPECIFIC EMBODIMENTS

The organothiophosphorus compounds contemplated herein are the S,S,S-trialkylphosphorotrithioites and other organothiophosphorous pesticides, which have a malodorous, mercaptan odor that tends to develop during shipment and storage. These compounds have utility as nematocides, insecticides, and cotton defoliants. Their use, however, is somewhat hampered by their malodorous nature.

Non-limiting examples of phosphorotrithioites contemplated herein are:

S,S,S-trimethylphosphorotrithioite,
S,S,S-triethylphosphorotrithioite,
S,S,S-tripropylphosphorotrithioite,
S,S,S-tributylphosphorotrithioite,
S,S,S-triamylphosphorotrithioite,
S,S,S-trihexylphosphorotrithioite,
S,S,S-trioctylphosphorotrithioite,
S,S,S-tributylphosphorotrithioite,
O,O-dimethylphosphorodithioate of diethylmercaptosuccinate,
O,O-diethyl-S-(2-ethylthioethyl)phosphorodithioate, and
O-ethyl-S,S-dipropylphosphorodithioate.

The ketones used to stabilize the organothiophosphorous pesticides in accordance with this invention are the $C_3$–$C_{10}$ aliphatic ketones and the $C_6$–$C_{10}$ cycloaliphatic ketones. Also contemplated are the cyclic diketones and their halogenated derivatives. Non-limiting examples of the contemplated ketones are acetone, methyl ethyl ketone, methyl vinyl ketone, methyl isobutyl ketone, ethyl amyl ketone, methyl heptyl ketone. cyclohexanone, cyclohexenone, mesityl oxide, isophorone, benzoquinone, and chloranil.

The amount of ketone used is a minor stabilizing amount. In general, based upon the weight of the organothiophosphorous compound, this will be between about 0.1 weight percent and about 10 weight percent, preferably between about 0.5 weight percent and about 7 weight percent.

The compositions of the present invention may be used in various ways to achieve the desired action according to the particular organothiophosphorus compound used. They can be applied as dusts, as liquid sprays, or as gas-propelled sprays and can contain, in addition to a carrier, additives such as emulsifying agents, gases compressed to the liquid state, other stabilizers and the like. A wide variety of liquid and solid carriers can be used in the compositions embodied in this invention. Non-limiting examples of the liquid carriers include water; organic solvents such as alcohols, ketones, amides, and esters; mineral oils, such as kerosene, light oils, and medium oils; and vegetable oils such as cottonseed oil. Non-limiting examples of solid carriers include talc, bentonite, diatomaceous earth, pyrophyllite, Fuller's earth, gypsum, flours derived from cottonseeds and nutshells, attaclay (attapulgite) and various natural and synthetic clays having a pH not exceeding about 9.5.

In practice, the compositions according to the invention may be prepared in the form of concentrates which are diluted in the field to the concentration desired for application as pesticides or as plant growth regulants. For example, the concentrate mixture can be a wettable powder containing large amounts of the desired organothiophosphorus compound, a carrier, e.g. attapulgite or other clay, and wetting and dispersing agents. Such powders can be diluted prior to application by dispersing them in water to obtain a sprayable suspension containing the concentration of organothiophosphorous compound desired for application. Other concentrate mixtures can be solutions that can be later diluted, e.g. with kerosene. Thus, it is within the contemplation of this invention to provide such compositions containing from about 5–10% to about 85% by weight of the total composition of, for example, a phosphorotrithioite compound. Accordingly, depending upon whether it is ready for application or it is in concentrated form said contemplated compositions preferably contain between about 5% and 80% by weight of the composition of at least one phosphorotrithioite and a carrier, liquid or solid, as defined hereinbefore.

A particularly feasible form in which the S,S,S-trialkylphosphorotrithioites are packaged is the emulsifiable concentrate. Such concentrate is usually emulsified in water and sprayed on the area to be treated, usually by airplane. Typically, the emulsifiable concentrate contains, by weight of the composition, between about 25 weight percent and about 80 weight percent active ingredient, between about 5 weight percent and about 10 weight percent total of one or more anionic emulsifiers, and the balance, between about 10 weight percent and about 20 weight percent, aliphatic or aromatic hydrocarbon solvent.

EXAMPLE 1

Samples of an emulsifiable concentrate containing 75% weight S,S,S,-tributyl phosphorotrithioite (Merphos), 5% T-Mulz MLO, (phosphate ester emulsifier—Thompson-Hayward Co.,) and 2% Triton GR-7M (sodium dioctyl sulfo-succinate emulsifier—Rohm & Haas Co.,) and 18% wt. Tenneco 500/100 solvent (xylene-range aromatic solvent—Tenneco Oil Co.) were treated as follows. After addition of from 0.1% to 10% of additive, the samples were held at 50° C. and at room temperature in capped vials (20°–30° C.) and analyzed periodically for total mercaptans content (expressed as equivalent % butyl mercaptan.) The results are set forth in Table I.

TABLE 1

| | | % wt. mercaptans as butyl mercaptan | | | | | |
|---|---|---|---|---|---|---|---|
| | % wt. additive | Initial | 3 days 50° C. | Room temperature (20°–30° C.) | | | |
| Additive | | | | 2 wks. | 4 wks. | 6 wks. | 18 wks. |
| Acetone | 1 | 0.14 | 0.01 | 0.11 | 0.05 | 0.06 | 0.07 |
| Cyclohexanone | 1 | 0.04 | 0.08 | 0.13 | 0.12 | 0.06 | 0.12 |
| Isophorone | 1 | 0.05 | 0.21 | 0.23 | 0.22 | 0.11 | 0.07 |
| Mesityl oxide | 1 | 0.06 | 0.11 | 0.11 | 0.12 | 0.06 | 0.07 |
| Methyl ethyl ketone | 1 | 0.06 | 0.05 | 0.19 | 0.10 | 0.03 | 0.12 |
| Methyl isobutyl ketone | 1 | 0.07 | 0.18 | 0.21 | 0.20 | 0.08 | 0.10 |
| Benzaldehyde | 1 | 0.08 | 0.11 | 0.06 | 0.10 | 0.03 | 0.10 |
| Paraformaldehyde | 0.1 | 0.20 | 0.47 | 0.40 | 0.54 | 0.42 | 0.31 |
| None | 0 | 0.10 | 0.29 | 0.28 | 0.42 | 0.25 | 0.31 |

It was noted that certain ketones, particularly acetone and mesityl oxide, had equal or better suppressing effect on the release of mercaptan than benzaldehyde, which is a recognized mercaptan odor suppressor.

Commercial S,S,S-tributyl phosphorotrithioate (Merphos, a cotton defoliant) normally contains a trace of cuprous chloride as an anti-oxidant. The Merphos used in the above experiments contained 0.05% cuprous chloride.

EXAMPLE 2

In order to determine whether the cuprous chloride content of the commercial Merphos was having a catalytic effect on mercaptan suppression by the ketones, an additional sample of Merphos was obtained, containing no cuprous chloride. Samples of 75% Merphos concentrate (emulsifiable) containing commercial Merphos and cuprous chloride-free Merphos, were treated identically with ketones, and placed under test. The results are set forth in Table II.

TABLE II

| | | | Mercaptans (as % butyl mercaptans) found. | | |
|---|---|---|---|---|---|
| Additive | % wt. | % Cuprous chloride in Merphos used | Initial | 1 week 50° C. | 2 weeks Rm. Temp. | 12 weeks Rm. Temp. |
| Acetone | 2 | 0.05 | 0.1 | 0.13 | 0.04 | 0.01 |
| Mesityl oxide | 5 | 0.05 | 0.1 | 0.08 | 0.02 | 0.01 |
| Dihydropyran | 1 | 0.05 | 0.1 | 0.13 | 0.02 | 0.01 |
| None | 0 | 0.05 | 0.1 | 0.38 | 0.20 | 0.28 |
| Acetone | 2 | None | 0.1 | 0.15 | 0.16 | 0.05 |
| Mesityl oxide | 5 | None | 0.1 | 0.08 | 0.04 | 0.04 |
| Dihydropyran | 1 | None | 0.1 | 0.13 | 0.04 | 0.03 |
| None | 0 | None | 0.1 | 0.58 | 0.20 | 0.33 |

EXAMPLE 3

Formulated Merphos generates small amounts of mercaptan during storage, due to reaction with small amounts of water and hydroxyl-containing molecules. In order to compare the mercaptan-scavenging effects of acetone with and without possible catalysts present, a sample of an inert hydrocarbon solvent, toluene, was spiked with about 0.05 moles butyl mercaptan per liter. Sub-samples were spiked with acetone and additive combinations, and analyzed initially and after stated time periods at the stated temperatures. Results are set forth in Table III.

TABLE III

| | Toluene solutions, moles/liter | | | Butyl mercaptan found, moles/liter | | |
|---|---|---|---|---|---|---|
| Sample | Acetone | Acetic acid | Cuprous chloride | Butyl mercaptan | 2 hrs. 70° C. | 2 weeks 50° C. | 2 weeks room temp.* |
| A | 0.4 | — | — | 0.049 | 0.044 | 0.043 | 0.043 |
| B | 0.4 | 0.1 | — | 0.048 | 0.039 | 0.037 | 0.043 |
| C | 0.4 | 0.1 | 0.002 | 0.048 | 0.004 | 0.000 | 0.000 |
| D | 0.4 | — | 0.002 | 0.050 | 0.000 | 0.000 | 0.000 |
| E | None | — | — | 0.050 | 0.049 | 0.039 | 0.045 |

*20°–30° C.

It was evident that the mercaptan-scavenging effect of acetone was enhanced by the small addition of cuprous chloride.

EXAMPLE 4

A further series of tests was initiated, in which the effects of various potential catalysts, on the mercaptan-scavenging ability of 0.4 molar mesityl oxide in toluene, were compared. In this series, cuprous chloride and p-toluene sulfonic acid were the only materials tested which had a strong catalytic effect, although oil-soluble salts of copper, manganese, cobalt and iron had noticeable effects. Results are given in Table IV.

TABLE IV

| | Toluene solutions (molar concentrations) | | | | Butyl mercaptan found, moles/liter | | | |
|---|---|---|---|---|---|---|---|---|
| Sample | Mesityl Oxide | Catalyst | Conc. | Butyl Mercaptan | 20 hrs. 50° C. | 2 wks. 50° C. | 3 wks. Rm. Temp. | 6 wks. Rm. Temp. |
| A | 0.4 | NH4Cl | 0.004 | 0.047 | 0.050 | 0.036 | 0.050 | 0.042 |
| B | 0.4 | HCl* | 0.004 | 0.047 | 0.047 | 0.038 | 0.042 | 0.039 |
| C | 0.4 | Cu2Cl2 | 0.002 | 0.047 | 0.005 | 0.000 | 0.000 | 0.000 |
| D | 0.4 | Copper naphthenate (Cu) | 0.004 | 0.047 | 0.038 | 0.013 | 0.028 | 0.033 |
| E | 0.4 | Manganese Octate (Mn) | 0.004 | 0.047 | 0.030 | 0.003 | 0.025 | 0.021 |
| F | 0.4 | Zinc naphthenate (Zn) | 0.004 | 0.047 | 0.047 | 0.020 | 0.039 | 0.044 |
| G | 0.4 | Cobalt | | | | | | |

TABLE IV-continued

| | | | | | Butyl mercaptan found, moles/liter | | | |
|---|---|---|---|---|---|---|---|---|
| | | Toluene solutions (molar concentrations) | | | 20 hrs. | 2 wks. | 3 wks. | 6 wks. |
| Sample | Mesityl Oxide | Catalyst | Conc. | Butyl Mercaptan | 50° C. | 50° C. | Rm. Temp. | Rm. Temp. |
| | | naphthenate (Co) | 0.004 | 0.047 | 0.028 | 0.013 | 0.017 | 0.026 |
| H | 0.4 | Ferric (Fe) octoate | 0.004 | 0.047 | 0.040 | 0.013 | 0.025 | 0.028 |
| I | 0.4 | p-toluene sulfonic acid | 0.004 | 0.047 | 0.005 | 0.000 | 0.003 | 0.000 |
| J | 0.4 | None | | 0.047 | 0.047 | 0.026 | 0.036 | 0.051 |
| K | 0.0 | None | | 0.047 | 0.053 | 0.036 | 0.050 | 0.053 |

*37% aqueous HCl used

EXAMPLE 5

Additional ketones, and other additives, were evaluated with Merphos emulsifiable concentrate, as previously described, in which the technical Merphos used contained 0.05% cuprous chloride. Most, but not all ketones tested, were effective in keeping the mercaptans content to a low level. A tabulation of results is given in Table V.

TABLE V

| | | % wt. mercaptans, as butyl mercaptan. | | | | | | |
|---|---|---|---|---|---|---|---|---|
| | | | 50° C. | Room temperature (20°-30° C.) | | | | |
| Additive | % wt. | Initial | 1 wk. | 2 wks. | 4 wks. | 6 wks. | 8 wks. | 12 wks. |
| Chloranil | 1 | 0.07 | 0.06 | 0.00 | 0.00 | 0.07 | 0.06 | 0.17 |
| Benzaldehyde | 1 | 0.02 | 0.18 | 0.03 | 0.02 | 0.07 | 0.11 | 0.21 |
| Benzaldehyde | 2 | 0.02 | 0.11 | 0.03 | 0.00 | 0.07 | 0.06 | 0.19 |
| Oil of Bitter Almond* | 1 | 0.02 | 0.15 | 0.00 | 0.02 | 0.10 | 0.09 | 0.19 |
| Acetophenone | 1 | 0.02 | 0.15 | 0.07 | 0.08 | 0.09 | 0.12 | — |
| Cyclohexenone | 1 | 0.02 | 0.02 | 0.02 | 0.00 | 0.02 | 0.03 | 0.11 |
| Methyl ethyl ketone | 2 | 0.03 | 0.02 | 0.02 | 0.02 | 0.00 | 0.03 | 0.10 |
| Methyl vinyl ketone | 1 | 0.06 | 0.09 | 0.00 | 0.02 | 0.02 | — | 0.04 |
| Cyclohexanone | 10 | 0.04 | 0.02 | 0.19 | 0.18 | — | — | — |
| Isophorone | 10 | 0.02 | 0.10 | 0.05 | 0.05 | 0.09 | 0.09 | 0.17 |
| None | 0 | 0.04 | 0.29 | 0.07 | 0.11 | 0.23 | 0.22 | 0.30 |

*Naturally-occurring oil containing about 95% benzaldehyde and 2-4% HCN

Chloranil, cyclohexenone, methyl ethyl ketone, methyl vinyl ketone, and isophorone were effective suppressors of the build-up of mercaptan in the test samples.

EXAMPLE 6

Three formulations were prepared having the composition set forth in Table VI. All amounts are in weight percent. Formulation 1 contained acetone as the stabilizer and Formulation 2 contained mesityl oxide stabilizer. Formulation 3 was the control and contained no stabilizer.

TABLE VI

| | FORMULATION | | |
|---|---|---|---|
| COMPONENT | 1 | 2 | 3 |
| Merphos, 96%, tributyl phosphorotrithioite | 76.9 | 76.9 | 76.9 |
| T-Mulz MLO* | 5.0 | 5.0 | 5.0 |
| Triton GR 7M** | 2.0 | 2.0 | 2.0 |
| Acetone | 1.0 | — | — |
| Mesityl oxide | — | 5.0 | — |
| Tenneco 500/100 solvent*** | 15.1 | 11.1 | 16.1 |
| Totals | 100.0 | 100.0 | 100.0 |
| % butyl mercaptan, as prepared: | 0.00 | 0.00 | |
| as used: | 0.02 | 0.00 | 0.06 |

TABLE VI-continued

| | FORMULATION | | |
|---|---|---|---|
| COMPONENT | 1 | 2 | 3 |
| Flash-point, (tag Closed Cup) | 87° F. | 105° F. | 122° F. |

*Phosphate ester emulsifier, Thompson-Hayward Chemical Co.
**Emulsifier - 70% sodium dioctyl sulfo-succinate in aromatic solvent - Rohm & Haas Co.
***Aromatic petroleum solvent, xylene-range, specific gravity 0.870, distillation range 290°-340° F., Tenneco Oil Co.

EXAMPLE 7

The above formulations of Table VI were applied, diluted one pint per gallon in water, by airplane on cotton fields for defoliation of cotton. The formulations 1 and 2 gave little or no mercaptan odor in the vicinity of the spraying operation, during and after application. Formulation 3 gave a definite mercaptan odor in the vicinity of the spraying operation.

The mercaptan levels of formulations 1 and 2 were 0.02 and 0.00% wt. before they were added to the spray tank. At the time of preparation their levels were 0.00 and 0.00% respectively. Formulation 3 had mercaptan level of 0.05% at time of spraying.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A composition comprising an organothiophosphorus compound of the structure: $P(SR)_3$ wherein R is $C_1$–$C_8$ alkyl and a minor stabilizing amount of a $C_3$–$C_{10}$ aliphatic or cycloaliphatic ketone.

2. A composition of claim 1, wherein said organothiophosphorus compound is S,S,S,-tributyl phosphorotrithioite.

3. A composition of claim 2, wherein said ketone is acetone.

4. A composition of claim 2, wherein said ketone is mesityl oxide.

5. A composition of claim 2, wherein said ketone is cyclohexanone.

6. A composition of claim 2, wherein said ketone is methyl ethyl ketone.

7. A composition of claim 1, wherein said stabilizing amount of ketone is between about 0.1 and about 10 weight percent based on phosphorus compound.

8. A composition of claim 7, wherein said amount is between about 0.5 and about 7 weight percent.